US009809524B1

(12) United States Patent
Smits

(10) Patent No.: US 9,809,524 B1
(45) Date of Patent: Nov. 7, 2017

(54) PROCESS FOR THE PREPARATION OF 1-(3,5-DICHLORO-4-FLUORO-PHENYL)-2,2,2-TRIFLUORO-ETHANONE

(71) Applicant: SYNGENTA PARTICIPATIONS AG, Basel (CH)

(72) Inventor: Helmars Smits, Stein (CH)

(73) Assignee: Syngenta Participations, Basel (CH)

( * ) Notice: Subject to any disclaimer, the term of this patent is extended or adjusted under 35 U.S.C. 154(b) by 0 days.

(21) Appl. No.: 15/516,087

(22) PCT Filed: Oct. 8, 2015

(86) PCT No.: PCT/EP2015/073218
§ 371 (c)(1),
(2) Date: Mar. 31, 2017

(87) PCT Pub. No.: WO2016/058896
PCT Pub. Date: Apr. 21, 2016

(30) Foreign Application Priority Data

Oct. 14, 2014 (EP) ..................... 14188741

(51) Int. Cl.
C07C 45/00 (2006.01)
C07C 49/80 (2006.01)
C07C 45/63 (2006.01)
C07C 45/46 (2006.01)

(52) U.S. Cl.
CPC ............ *C07C 45/63* (2013.01); *C07C 45/004* (2013.01); *C07C 45/46* (2013.01); *C07C 49/80* (2013.01)

(58) Field of Classification Search
CPC ....... C07C 45/46; C07C 45/004; C07C 45/63; C07C 49/80
USPC ....................................... 568/323
See application file for complete search history.

(56) References Cited

FOREIGN PATENT DOCUMENTS

| CN | 103664511 A | 3/2014 |
|---|---|---|
| WO | 8704151 A1 | 7/1987 |
| WO | 2009070485 A1 | 6/2009 |
| WO | 2009126668 A2 | 10/2009 |
| WO | 2012035011 A1 | 3/2012 |

OTHER PUBLICATIONS

International Search Report and Written Opinion for PCT/EP2015/073218, dated Nov. 27, 2015.
Sott et al: "Synthesis of dioxin-like monofluorinated PCBs: for the use as internal standards for PCB analysis", Tetrahedron, Elsevier Science Publishers, Amsterdam, NL, vol. 64, No. 18, Jan. 5, 2008 (Jan. 5, 2008), pp. 4135-4142, XP022551930, ISSN: 0040-4020, DOI: 10. 1016/J. TET. 2008. 01. 003.
Narender, N. et al: "Liquid Phase Regioselective Bromination of Aromatic Compounds Over Hzsm-5 Catalyst", Synthetic Communication, vol. 30, No. 20, Oct. 1, 2000 (Oct. 1, 2000), pp. 3669-3675, XP055170314, ISSN: 0039-7911, DOI: 10. 1080/00397910008086993.
Extended European Search Report for EP14188741.4, dated Feb. 26, 2015.

(Continued)

*Primary Examiner* — Sikarl Witherspoon
(74) *Attorney, Agent, or Firm* — R. Kody Jones

(57) ABSTRACT

The invention relates to a process for the preparation of a compound of formula I comprising a) reacting a compound of formula II in the presence of magnesium or an organometallic reagent of formula III $R_1M^2X$ (III), wherein $R_1$ is $C_1$-$C_4$alkyl; $M^2$ is Li or Mg and X is halogen or absent; with a compound of formula IV $CF_3$—$C(O)$—$R_2$ (IV), wherein $R_2$ is halogen, hydroxyl, $C_1$-$C_4$alkoxy, (di-$C_1$-$C_4$alkyl) amino, $OC(O)CF_3$, phenoxy or $OM^1$; wherein $M^1$ is Lithium, Magnesium, Sodium or Potassium; to a compound of formula V, and b) reacting the compound of formula V with alkali metal fluoride in the presence of catalytic amounts of a phase transfer catalyst in the presence of a polar solvent to the compound of formula I.

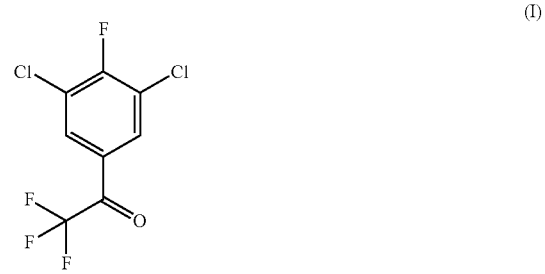

(I)

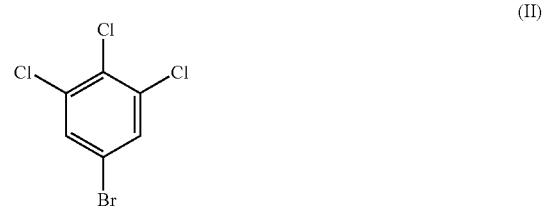

(II)

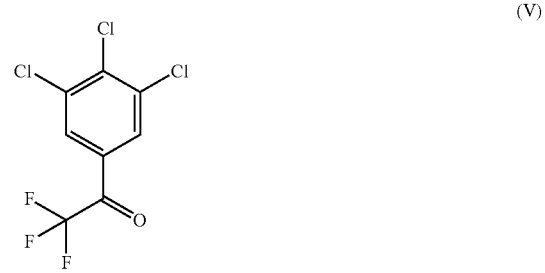

(V)

8 Claims, No Drawings

(56) References Cited

OTHER PUBLICATIONS

Miller, Max W. et al: "Anticoccidial derivatives of 6-azauracil. 3. Synthesis, high activity, and short plasma half-life of 1-phenyl-6-azauracils containing sulfonamide substituents", Journal of Medicinal Chemistry, vol. 23, No. 10, Oct. 1, 1980 (Oct. 1, 1980) , pp. 1083-1087, XP055170315, ISSN: 0022-2623, DOI: 10.1021jjm00184a005.

PROCESS FOR THE PREPARATION OF 1-(3,5-DICHLORO-4-FLUORO-PHENYL)-2,2,2-TRIFLUORO-ETHANONE

RELATED APPLICATION INFORMATION

This application is a 371 of International Application No. PCT/EP2015/073218, filed Oct. 8, 2015, which claims priority to EP Application No. 14188741.4, filed Oct. 14, 2014, the contents of which are incorporated by reference herein.

The present invention relates to the preparation of 1-(3,5-dichloro-4-fluoro-phenyl)-2,2,2-trifluoro-ethanone using 5-bromo-1,2,3-trichloro-benzene as a starting material.

1-(3,5-dichloro-4-fluoro-phenyl)-2,2,2-trifluoro-ethanone is an important intermediate for the preparation of pesticidally active isoxazoline-substituted benzamides as for example disclosed in EP 1932836A1.

1-(3,5-dichloro-4-fluoro-phenyl)-2,2,2-trifluoro-ethanone can be advantageously prepared by using 5-bromo-1,2,3-trichloro-benzene as a starting material. 5-bromo-1,2,3-trichloro-benzene can be prepared as described in Narander, N.; Srinivasu, P.; Kulkarni, S. J.; Raghavan, K. V. Synth. Comm. 2000, 30, 3669 and Sott, R.; Hawner, C.; Johansen, J. E. Tetrahedron 2008, 64, 4135. 3-Trifluoromethyl chalcones can be prepared according to methods disclosed in WO 2009/126668.

The synthesis of aryltrifluoromethyl ketones by reacting derivatives of trifluoroacetic acid with organometallic reagents derived from haloarenes is well known and for example described in WO 2012/120135 for the preparation of 2,2,2-trifluoro-1-(3,4,5-trichlorophenyl)ethanone. For the synthesis of 1-(3,5-dichloro-4-fluoro-phenyl)-2,2,2-trifluoro-ethanone the corresponding starting material is 5-bromo-1,3-dichloro-2-fluoro-benzene. However, this substance is difficult to prepare in particular on a large scale with the only described synthesis being an inefficient multistep approach described in Miller, M. W.; Mylari, B. L.; Howes, H. L.; Figdor, S. K.; Lynch, M. J.; Lynch, J. E.; Koch, R. C. J. Med. Chem. 1980, 23, 1083, CN 101177379, WO 2009/070485 and CN 103664511 (Scheme 1).

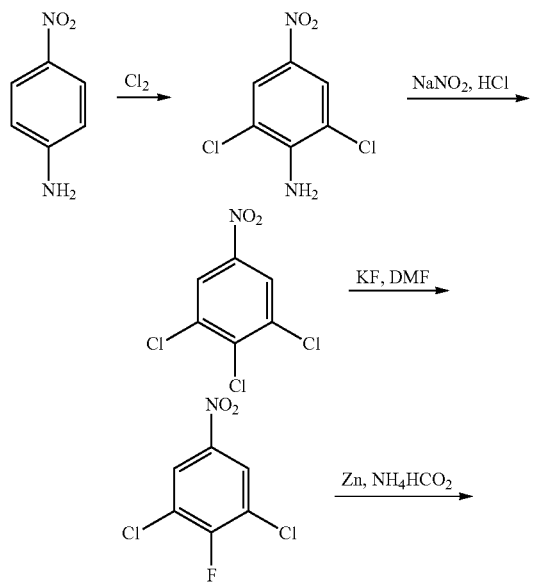

Scheme 1

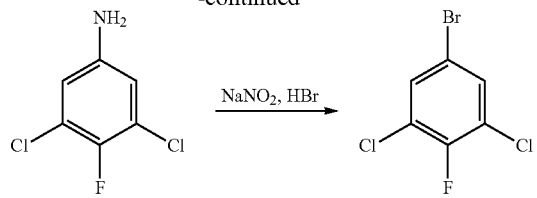

Therefore, it is highly desirable to prepare 1-(3,5-dichloro-4-fluoro-phenyl)-2,2,2-trifluoro-ethanone from the more easily accessible 2,2,2-trifluoro-1-(3,4,5-trichlorophenyl)ethanone. Surprisingly, it was found that reacting 2,2,2-trifluoro-1-(3,4,5-trichlorophenyl)ethanone with potassium fluoride in the presence of a phase transfer catalyst and a polar solvent provided the desired 1-(3,5-dichloro-4-fluoro-phenyl)-2,2,2-trifluoro-ethanone. While such nucleophilic aromatic substitution reactions are well known for nitroaromatic compounds (as for example disclosed in WO 92/00270) there is no prior art describing comparable reactions with trifluoromethyl ketones since this group is in general not known to be a sufficiently strong activating group.

It is therefore the object of the present invention to provide a process for the preparation of 1-(3,5-dichloro-4-fluoro-phenyl)-2,2,2-trifluoro-ethanone using 5-bromo-1,2,3-trichloro-benzene as an intermediate. The process according to the invention is characterized by a reduced number of reaction steps and high selectivity and yield.

Thus, according to the present invention, there is provided a process for the preparation of the compound of formula I

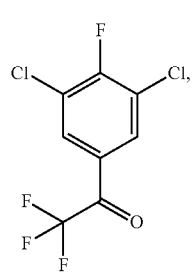

(I)

comprising
a) reacting the compound of formula II

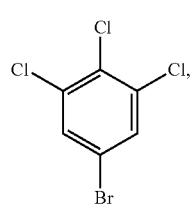

(II)

in the presence of magnesium or an organometallic reagent of formula III

 (III), wherein
$R_1$ is $C_1$-$C_4$alkyl;
$M^2$ is Lithium or Magnesium and
X is halogen or absent;

with a compound of formula IV $$CF_3—C(O)—R_2 \quad (IV),$$

wherein
$R_2$ is halogen, hydroxyl, $C_1$-$C_4$alkoxy, (di-$C_1$-$C_4$alkyl)amino, $OC(O)CF_3$, phenoxy or $OM^1$; wherein $M^1$ is Lithium, Magnesium, Sodium or Potassium; to the compound of formula V, (V)

and
b) reacting the compound of formula V with an alkali metal fluoride in the presence of catalytic amounts of a phase transfer catalyst in the presence of a polar solvent to the compound of formula I.

The alkyl groups occurring in the definitions of the substituents can be straight-chain or branched and are, for example, methyl, ethyl, n-propyl, isopropyl, n-butyl, sec-butyl, iso-butyl or tert-butyl. Alkoxy is, for example, methoxy, ethoxy, propoxy, i-propoxy, n-butoxy, isobutoxy, sec-butoxy and tert-butoxy. The following scheme describes the reactions of the invention in more detail.

Scheme 2

Step a)
The compound of formula V can be prepared by reacting a compound of formula II first with magnesium then with a compound of formula IV $$CF_3—C(O)R_2 \quad (IV),$$

wherein $R_2$ is halogen, hydroxyl, $C_1$-$C_4$alkoxy, (di-$C_1$-$C_4$alkyl)amino, $OC(O)CF_3$, phenoxy or $OM^1$; wherein $M^1$ is Lithium, Magnesium, Sodium or Potassium. Alternatively, the compound of formula V can be prepared by reacting a compound of formula II first with an organometallic reagent of formula III $$R_1—M^2X \quad (III),$$

wherein
$R_1$ is $C_1$-$C_4$alkyl;
$M^2$ is Lithium or Magnesium and
X is halogen or absent; and then with the compound of formula IV $$CF_3—C(O)R_2 \quad (IV),$$

wherein $R_2$ is halogen, hydroxyl, $C_1$-$C_4$alkoxy, (di-$C_1$-$C_4$alkyl)amino, $OC(O)CF_3$, phenoxy or $OM^1$; wherein $M^1$ is Lithium, Magnesium, Sodium or Potassium. The compound of formula III is preferably used in form of a complex with LiCl.

Typically the reaction is performed in an aprotic organic solvent. Suitable solvents include but are not limited to organic ethers such as tetrahydrofuran, 2-methyl-tetrahydrofuran, 1,4-dioxane, diethyl ether, t-butylmethyl ether and hydrocarbons such as toluene, benzene, hexane and cyclohexane. The reaction can be carried out at a temperature from −80° C. to 50° C., preferably from −20° C. to 25° C.
Step b):

The compound of formula I can be prepared by reaction of a compound of formula V with an alkali metalfluoride in the presence of a phase transfer catalyst. Suitable metal fluorides include KF, LiF and NaF. Suitable phase transfer catalysts include phosphonium salts of general formula $(R_3)_4PX$ and ammonium salts of general formula $(R_3)_4NX$ where $R_3$ is $C_1$-$C_4$alkyl or phenyl and X is halogen. Phosphonium salts are preferred.

Typically the reaction is performed in an organic solvent or mixtures thereof. Suitable solvents are polar in nature and include, but are not limited to sulfolane, dimethylformamide and dimethylsulfoxide.

The reaction can be carried out at a temperature from 100° C. to 250° C., preferably from 120° C. to 160° C.

A preferred embodiment of the process of the invention comprising
a) reacting the compound of formula II (II)

in the presence of an organometallic reagent of formula III $$R_1—M^2X \quad (III),$$

wherein
$R_1$ is $C_1$-$C_4$alkyl;
$M^2$ is Lithium or Magnesium and
X is halogen or absent;
with a compound of formula IV $$CF_3—C(O)—R_2 \quad (IV),$$

wherein $R_2$ is halogen, hydroxyl, $C_1$-$C_4$alkoxy, (di-$C_1$-$C_4$alkyl)amino, OC(O)CF$_3$, phenoxy or OM$^1$; wherein M$^1$ is Lithium, Magnesium, Sodium or Potassium;
to the compound of formula V,

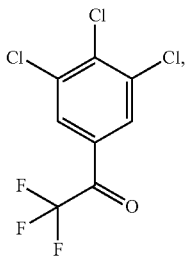

and
b) reacting the compound of formula V with metal fluoride selected from KF, LiF and NaF in the presence of catalytic amounts of a phase transfer catalyst selected from the group consisting of phosphonium salts of general formula $(R_3)_4$PX and ammonium salts of general formula $(R_3)_4$NX wherein $R_3$ is $C_1$-$C_4$alkyl or phenyl and X is halogen; in the presence of a polar solvent selected from the group consisting of sulfolane, dimethylformamide and dimethylsulfoxide, to the compound of formula I. In said preferred embodiment of the invention, the organometallic reagent is isopropylmagnesiumchloride complexed with LiCl.

PREPARATORY EXAMPLES

Example 1: Preparation of 2,2,2-trifluoro-1-(3,4,5-trichlorophenyl)ethanone of Formula V

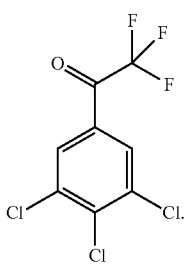

To a solution of 5-bromo-1,2,3-trichloro-benzene (220 g, 811 mmol) in tetrahydrofuran (1600 ml) was added 1.3 M iPrMgCl.LiCl in THF (1250 ml, 1622 mmol) slowly at 20° C. The reaction mixture was stirred for 2 hours and cooled to 0° C. Methyl 2,2,2-trifluroacetate (314.8 g, 2434 mmol) was added slowly and the reaction mixture was stirred at ambient temperature for 1 hour. The reaction mixture was cooled to 0° C. and 2.0 M HCl (810 ml, 1622 mmol) was added dropwise during 30 min. The resulting mixture was diluted with ethyl acetate, the organic layer was washed with brine, dried over anhydrous MgSO$_4$ and evaporated under reduced pressure. The crude product was dissolved in a minimum amount of cyclohexane and the solution was cooled to −10° C. The formed precipitate was filtered off to afford 2,2,2-trifluoro-1-(3,4,5-trichlorophenyl)ethanone (122 g) as a yellow solid. The filtrate was diluted with cyclohexane and washed twice with acetonitrile. Cyclohexane phase was evaporated under reduced pressure and the residue was dissolved in a minimum amount of cyclohexane. The solution was cooled to −10° C. and another portion of 2,2,2-trifluoro-1-(3,4,5-trichlorophenyl)ethanone (35 g) was filtered off.
$^1$H NMR (400 MHz, CDCl$_3$) δ8.07-8.05 (m, 2H).

Example 2: Preparation of 1-(3,5-dichloro-4-fluoro-phenyl)-2,2,2-trifluoro-ethanone of formula I

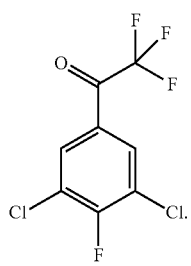

To a solution of 2,2,2-trifluoro-1-(3,4,5-trichlorophenyl)ethanone (1.0 g, 3.6 mmol) in sulfolane (3 ml) was added dry potassium fluoride (0.35 g, 4.32 mmol) and tetraphenylphosphonium bromide (0.015 g, 0.036 mmol). The resulting reaction mixture was stirred at 160° C. for 5 hours. The reaction mixture was distilled under reduced pressure. Fractions containing the product were further purified with silica gel chromatography (eluting with pure heptane) to afford 1-(3,5-dichloro-4-fluoro-phenyl)-2,2,2-trifluoro-ethanone (0.571 g) as a colorless oil and a mixture of ketone and hydrate forms (ca 3:1).
$^{19}$F NMR (400 MHz, CDCl$_3$) δ−71.5, −84.7, −102.4, −112.9.

The invention claimed is:
1. A process for the preparation of the compound of formula I

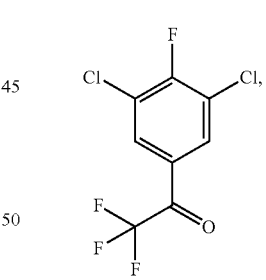

comprising
a) reacting the compound of formula II

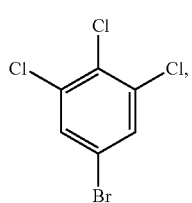

in the presence of magnesium or an organometallic reagent of formula III

 (III), wherein
$R_1$ is $C_1$-$C_4$alkyl;
$M^2$ is Lithium or Magnesium and
X is halogen or absent;
with a compound of formula IV $CF_3$—C(O)—$R_2$ (IV), wherein $R_2$ is halogen, hydroxyl, $C_1$-$C_4$alkoxy, (di-$C_1$-$C_4$alkyl)amino, OC(O)$CF_3$, phenoxy or $OM^1$; wherein $M^1$ is Lithium, Magnesium, Sodium or Potassium;
to the compound of formula V,

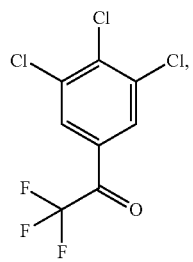 (V)

and
b) reacting the compound of formula V with an alkali metal fluoride in the presence of catalytic amounts of a phase transfer catalyst in the presence of a polar solvent to the compound of formula I.

2. A process according to claim 1, comprising
a) reacting the compound of formula II

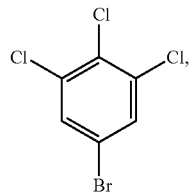 (II)

in the presence of an organometallic reagent of formula III

 (III)

wherein
$R_1$ is $C_1$-$C_4$alkyl;
$M^2$ is Lithium or Magnesium and
X is halogen or absent.

3. A process according to claim 2, wherein the organometallic reagent is isopropylmagnesiumchloride complexed with LiCl.

4. A process according to claim 1, wherein the alkali metal fluoride is selected from KF, LiF and NaF.

5. A process according to claim 1, wherein the phase transfer catalyst is selected from the group consisting of phosphonium salts of general formula $(R_3)_4PX$ and ammonium salts of general formula $(R_3)_4NX$ wherein $R_3$ is $C_1$-$C_4$alkyl or phenyl and X is halogen.

6. A process according to claim 1, wherein the polar solvent is selected from the group consisting of sulfolane, dimethylformamide and dimethylsulfoxide.

7. A process according to claim 1, comprising
a) reacting the compound of formula II

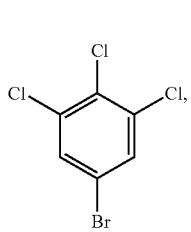 (II)

in the presence of an organometallic reagent of formula III

 (III)

wherein
$R_1$ is $C_1$-$C_4$alkyl;
$M^2$ is Lithium or Magnesium and
X is halogen or absent;
with a compound of formula IV $CF_3$—C(O)—$R_2$ (IV), wherein $R_2$ is halogen, hydroxyl, $C_1$-$C_4$alkoxy, (di-$C_1$-$C_4$alkyl)amino, OC(O)$CF_3$, phenoxy or $OM^1$; wherein $M^1$ is Lithium, Magnesium, Sodium or Potassium;
to the compound of formula V,

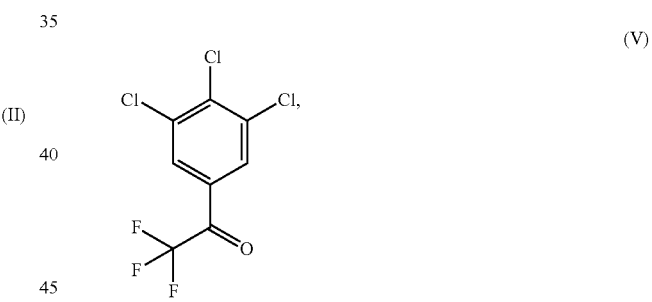 (V)

and
b) reacting the compound of formula V with an alkali metal fluoride selected from KF, LiF and NaF in the presence of catalytic amounts of a phase transfer catalyst selected from the group consisting of phosphonium salts of general formula $(R_3)_4PX$ and ammonium salts of general formula $(R_3)_4NX$ wherein $R_3$ is $C_1$-$C_4$alkyl or phenyl and X is halogen; in the presence of a polar solvent selected from the group consisting of sulfolane, dimethylformamide and dimethylsulfoxide, to the compound of formula I.

8. A process according to claim 7, wherein the organometallic reagent is isopropylmagnesiumchloride complexed with LiCl.

* * * * *